United States Patent [19]

Adams et al.

[11] Patent Number: 4,908,210
[45] Date of Patent: Mar. 13, 1990

[54] LACTYLIC SALT TABLET FORMULATIONS AND TABLETS

[75] Inventors: Michael W. Adams, Bluff City; Shabir Z. Masih, Kingsport, both of Tenn.

[73] Assignee: Eastman Kodak Company, Rochester, N.Y.

[21] Appl. No.: 264,120

[22] Filed: Oct. 28, 1988

[51] Int. Cl.$^4$ .................. A61K 47/00; A61K 9/50
[52] U.S. Cl. .................. 424/439; 424/465; 424/489; 424/502
[58] Field of Search ........... 424/489, 502, 464, 465, 424/439

[56] References Cited

U.S. PATENT DOCUMENTS

| | | | |
|---|---|---|---|
| 2,634,234 | 4/1953 | Kuhrt | 202/52 |
| 2,634,278 | 4/1953 | Kuhrt | 260/410.7 |
| 2,634,279 | 4/1953 | Kuhrt | 260/410.7 |
| 4,229,480 | 10/1980 | Suggs et al. | 426/653 |
| 4,239,786 | 12/1980 | Gilmore et al. | 426/602 |
| 4,310,557 | 1/1982 | Suggs et al. | 426/96 |
| 4,310,561 | 1/1982 | Buddemeyer et al. | 426/601 |
| 4,315,041 | 2/1982 | Fukuda et al. | 426/601 X |
| 4,363,826 | 12/1982 | Fukuda et al. | 426/653 |
| 4,492,714 | 1/1985 | Cooper | 426/602 |
| 4,668,519 | 5/1987 | Dartey et al. | 426/548 |

Primary Examiner—Thurman K. Page
Attorney, Agent, or Firm—John F. Stevens; William P. Heath, Jr.

[57] ABSTRACT

Disclosed are tabletable formulations and tablet produced therefrom. The formulations comprise an active ingredient such as a medicament or nutrient, and an improved lubricant which comprises monoglycerides, propylene glycol monoesters, and a salt of a fatty acid ester of lactylic acid.

6 Claims, 2 Drawing Sheets

LACTYLIC SALT TABLET FORMULATIONS AND TABLETS

TECHNICAL FIELD

This invention relates to tablets such as pharmaceutical tablets which contain lubricants and to tabletable formulations used in the preparation of such tablets. The lubricant used in this invention improves flow characteristics and processability of powder formulations, and provides improved disintegration and dissolution characteristics of tablets.

BACKGROUND OF THE INVENTION

Lubricants have a number of functions in tablet manufacture. They prevent adhesion of the tablet material to the surface of dies and punches, reduce interparticulate friction, facilitate the ejection of tablets from the die cavities, and may improve the rate of flow of the tabletable formulation. Commonly used lubricants include talc, magnesium stearate, calcium stearate, stearic acid, and hydrogenated vegetable oils. Most lubricants are used in concentrations from 0.25% to 5.0%, dependent upon the lubricant and tablet granulation. Lubricants are in most cases hydrophobic materials. Poor selection or excessive amounts can result in waterproofing the tablets, resulting in poor tablet disintegration and dissolution of the active ingredient.

The addition of a proper lubricant is highly desirable if the material to be tableted tends to stick to punches and dies. Immediately after compression, most tablets have the tendency to expand and will bind and stick to the side of the die. The choice of the proper lubricant will effectively overcome this. Since they are only required to act at the tooling/material interface, lubricants are generally incorporated at the end of any pre-compression stage and overmixing avoided, so that the maximum amount is retained on the surface of the particles. Lubricants act by interposing an intermediate layer between the tablet constituents and the die wall, which yields preferentially when the tablet surface moves relative to the die on compression and on ejection.

A problem in the preparation of a water-soluble tablet is the selection of a satisfactory lubricant. Soluble lubricants reported to be effective include sodium benzoate and sodium acetate, sodium chloride, leucine, and high molecular weigh poly(ethylene glycol). However, it has been suggested that formulations used to prepare water-soluble tablets may represent a number of compromises between compression efficiency and water solubility. While magnesium stearate is one of the most widely used lubricants, its hydrophobic properties can retard disintegration and dissolution.

The present invention utilizes a lubricant having the lubricating properties of magnesium stearate without its disadvantages. This lubricant composition is superior to magnesium stearate in promoting proper flow of tablet formulations from the hopper, maintaining an acceptable tablet hardness at various concentrations, maintaining tablet hardness at low compression force settings, and good disintegration and dissolution characteristics.

U.S. Pat. No. 4,310,557 relates to the lubricant formulation used in the present invention as a food emulsifier.

DESCRIPTION OF THE INVENTION

Figure 1:
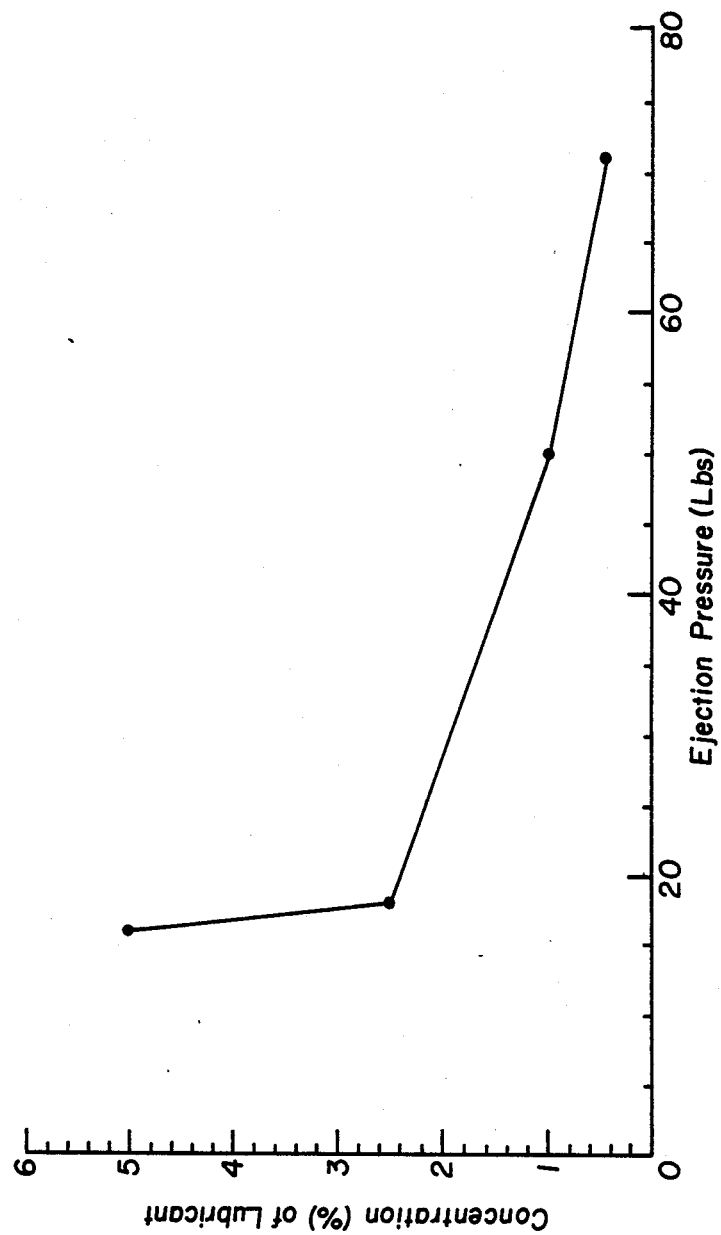
FIG. 1 is a graph showing concentration of Lubricant A versus ejection pressure measured on the tablet forming machine.

According to the present invention, there is provided a tabletable powder formulation comprising an active ingredient and about 0.5 to about 5.0%, based on the formulation weight of a lubricant which comprises
(a) about 20–40% by weight (preferably about 25–35%) of monoglycerides having an iodine value of about 2–15,
(b) about 40–70% by weight (preferably about 50–60%) of propylene glycol monoesters, and
(c) about 5–20% by weight (preferably about 12–18%) of a salt of at least one fatty acid ester of lactylic acid having 8-22 carbon atoms.

Also, according to the invention there are provided tablets comprising the formulations described above.

Preferably, the lubricant is present in an amount of about 0.6 to about 4.5 and most preferably, about 1.0 to about 3.0%, based on the total formulation weight. Preferably also, the lubricant comprises a flow agent such as fumed silica to prevent caking.

The monoglycerides having iodine value of about 2-15 have the general formula

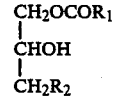

wherein $R_1$ is the residue of a straight chain fatty acid having from 8 to 22 carbon atoms and $R_2$ is OH or H. They are prepared by reacting glycerine with straight chain fatty acids such as those found in vegetable oils and animal fats having from 8 to 22 carbon atoms, and saturated to an extend to result in iodine value of about 2-15. Such monoglycerides are commercially available, for examples. Myverol 18-06 monoglycerides, from Eastman Chemical Products, Inc. The monoglycerides may be made by esterifying various fatty acids, and then blending to obtain the desired iodine number. On the other hand, acids with the proper degree of saturation may be selected to result in an iodine value of about 2-15.

The propylene glycol monoesters useful in accordance with the present invention have the general formula

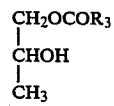

wherein $R_3$ is the residue of a straight chain saturated fatty acid having 8 to 22 carbon atoms. Preferably, $R_3$ is the residue of stearic acid, palmitic acid or a blend thereof. The propylene glycol monoesters are prepared by reacting propylene glycol with straight chain fatty acids such as those found in vegetable oils and animal fats having from 8 to 22 carbon atoms. Preferred monoesters include Myverol P-06 distilled propylene glycol monoesters, a product of Eastman Chemical products, Inc.

Salts of fatty acid esters of lactylic acid having 8-22 carbon atoms are well known and available commercially. Potassium and sodium stearoyl lactylate are examples of suitable salts. Sodium stearoyl lactylate is preferred.

As a practical matter, the monoglycerides and propylene glycol monoesters referred to above may contain diesters, triesters, unreacted material, and the like. It is preferred, however, that they be of a purity of at least 60% and most preferably, at least 90%. Such formulations conventially contain such material even though they are commonly referred to in the art as monoglycerides and monoesters.

The monoglycerides and monoesters of this invention are made in accordance with well-known procedures. One conventional procedure is the direct esterification of one or more fatty acids with glycerol or propylene glycol followed preferably by distillation to obtain a high purity product containing one or more monoester. Other procedures for the preparation of distilled, high purity monoglyceride products are disclosed in U.S. Pat. Nos. 2,634,234; 2,634,278 and 2,634,279, to Kuhrt. Such distilled monoester products usually contain monoesters at a concentration of at least about 90% by weight.

A preferred saturated monoester is a distilled monoester product made from fully hydrogenated lard with an iodine value in a range from about 0.4 to about 1. Preferred monoester products include the distilled monoester products made from fats and oils such as tallow palm oil, cottonseed oil, soybean oil, peanut oil, sesame oil, and the like.

The lubricant according to this invention may be prepared by melt blending the ingredients until a homogeneous mass is obtained and then forming a powder from the mass. Melt blending may be accomplished by individually maintaining or raising the temperatures of the compounds to a point above their respective melting temperatures so each is a molten mass and then thoroughly blending, or by mixing the ingredients at room temperature and then raising the temperature of the mixture at least to the melting point of the highest-to-melt ingredient followed by thoroughly blending to form a homogeneous mass. Preferably, melt blending is accomplished at a temperature of between about 80° C. and 120° C. Powdering may be accomplished by conventional means such as, for example, spray chilling, freezing and pulverizing, or by any other means known in the art. Laboratory experiments indicate that the quality of product produced on small scale by powdering in a blender using dry ice is quite satisfactory. Such powdering is accomplished by first heating a mixture of the selected ingredients until a molten or liquified mass is formed, and then rapidly stirring until the mass is homogenized. For example, 100 grams of molten mixture in a 250 ml beaker may be stirred until the mixture is found to be homogenous. The mixture may then be poured out and cooled until solidified, typically for about 3-4 hours at room temperature. The solid may then be powdered in a high speed stirring device such as a Waring Blendor using dry ice. The dry ice is subsequently evaporated and the powder residue sieved to an approximate size of 50-300 microns. The powder is white, free flowing, and the particles consist essentially of a homogeneous blend of the monoglycerides, propylene glycol monoesters and salt of fatty acid ester of lactylic acid.

The active ingredient of the powder formulation adapted to be formed into the tablets in accordance with this invention generally is an orally administratable medicament, nutrient, or the like. The powder may include conventional additives. Generally, any tabletable powder may be used, and it is normally of a grain size within the range of about 200 to about 500 microns. Active ingredients of special interest are aspirin and acetaminophren.

Examples of conventional additives include lubricants, diluents, compression agents, e.g. microcrystalline cellulose (MCC), and the like, which are well known to those skilled in the art.

The formulations of the present invention may be easily prepared using powder blending techniques well known to those skilled in the art. It is preferred that all the ingredients except the lubricant be blended first, and the lubricant be charged into the preblended mixture near the end of the blending process.

The following examples are submitted for a better understanding of the invention.

| Lubricant % by Weight of Lubricant | A | B | C | D |
|---|---|---|---|---|
| Monoglycerides | 30 | 22 | 38 | 33 |
| Propylene Glycol Monoesters | 55 | 68 | 42 | 62 |
| Sodium Stearoyl Lactylate | 15 | 10 | 20 | 5 |

In the lubricants described above, the monoglycerides are described as distilled monoglycerides having an iodine value of about 2 and a di- and triglyceride content of less than about 10%. This monoglyceride is commercially available from Eastman Chemical Products, Inc. as Myverol ® 18-06 monoglyceride.

In the composition described above, the propylene glycol monoesters are Myverol ® P-06 distilled propylene glycol monoesters, a product of Eastman Chemical Products, Inc.

Salts of fatty acid esters of lactylic acid employed in the invention are well known in the art and available commercially. They may be prepared by reacting lactylic acid with acids by known conventional condensation processes, such as those disclosed in U.S. Pat. No. 2,733,252, incorporated herein by reference. Illustrative of such salts are alkali, alkaline earth, ammonium, and in particular, the sodium, potassium, and calcium salts of fatty acid esters wherein the fatty acid contains 14 to 22 carbon atoms. Such fatty acids include palmitic, stearic, oleic and the like. Particularly preferred are sodium stearoyl-2-lactylate and calcium stearoyl-2-lactylate.

Tablet cores are produced on a Manesty 16-station Beta Press. Evaluation of Lubricant A at various levels is accomplished using the materials listed in Table I. Comparison of Lubricant A to magnesium stearate is performed using a table formulation consisting of aspirin crystals (#40 mesh), dicalcium phosphate, and microcrystalline cellulose. Blending is performed in a Patterson-Kelly Company twin shell rotary blender, hardness determinations on a Key International Hardness Tester, and disintegration and dissolution testing on Hanson equipment as described in the United States Pharmacopeia (USP) XXI. Liquid chromotography analysis is performed on a Waters QA-1. Dissolution data from the LC is processed on an IBM XT personal computer using a Lotus Macro and Statgraphics 2.6 software. Friability of tablets is measured on apparatus described in USP well known to those skilled in the art. Any other tests mentioned herein with respect to powder and tablet properties are found in USP.

The formulation listed in Table I is used to evaluate the effectiveness of Lubricant A as a lubricating agent. All the ingredients, less Lubricant A, are dry blended for ten minutes, then five additional minutes with the Lubricant A. The formulation used to evaluate magnesium stearate versus Lubricant A is listed in Table II. The dry blending is done as described above.

The formulation listed in Table I is tableted using constant machine settings. Lubricant A is varied in concentration, using levels of 1.0%, 2.5% and 5.0%, as well as the indicated 0.45%, and the concentration of acetylsalicylic acid is adjusted to make a total of 100%. Tablet weight is maintained at 400 milligrams, and the final compression held constant at 8,000 pounds of force. Tablet hardness is 12.0, 12.4, 10.8 and 10.0 Kilopons, respectively. The formulation listed in Table II is prepared in order to determine the effect of the lubricant on a slower dissolving aspirin matrix. The purpose of this is to magnify any differences in release profiles for tablets produced using magnesium stearate and Lubricant A. The tablet weights are held constant, but the final compression varied to maintain constant tablet hardness.

The tablets prepared using various levels of Lubricant A are disintegration tested by placing the tablets in 900 milliliters of water maintained at 37° C. No dissolution tests are performed on this particular formulation due to the rate at which the tablets dissolve. Disintegration of the tablets listed in Table II are performed in 900 milliliters of pH 1.2 phosphate buffer solution maintained at 37° C. Dissolution testing is performed in 900 milliliters of the same solution described above with a paddle speed of 100 rpm and sampling interval of 15 minutes until complete dissolution of the tablet is observed.

Lubricant A is an acceptable lubricating agent as evidenced by the ejection pressures for the increasing concentrations (FIG. 1). As the concentration of the Lubricant A is increased, the ejection pressure is reduced. The ideal use level of Lubricant A for this particular tablet formulation would probably be 1-2%. The tablet hardness is not adversely effected by the increasing levels of Lubricant A as seen with other lubricating agents such as magnesium stearate. Disintegration of the tablets is not effected by the level of Lubricant A. The 0.45% and 5.0% Lubricant A tablets begin disintegrating immediately upon addition to water and were completely disintegrated within one minute.

The comparison of Lubricant A to magnesium stearate is performed at a level of 2.0% for both lubricants. A tablet with no lubricant is also produced from this formulation as a control. Ejection pressures and tablet hardness are listed in Table III. The final compression required to obtain tablets of similar hardness is much lower for Lubricant A than magnesium stearate. This could have a tremendous impact on the lifetime of tooling and energy requirements for a tableting press. Lubricant A increases the flowability of the tableting formulation due to its higher bulk density. The magnesium stearate has a very low bulk density and, therefore, does not contribute towards increasing the flowability of the tableting formulation.

Disintegration is performed on six tablets from each formulation. The tablets with no lubricant and those containing Lubricant A completely disintegrate within 18 minutes from time of addition to the buffer solution. The tablets containing 2% magnesium stearate take 80 minutes to reach 100% disintegration.

Figure 2:
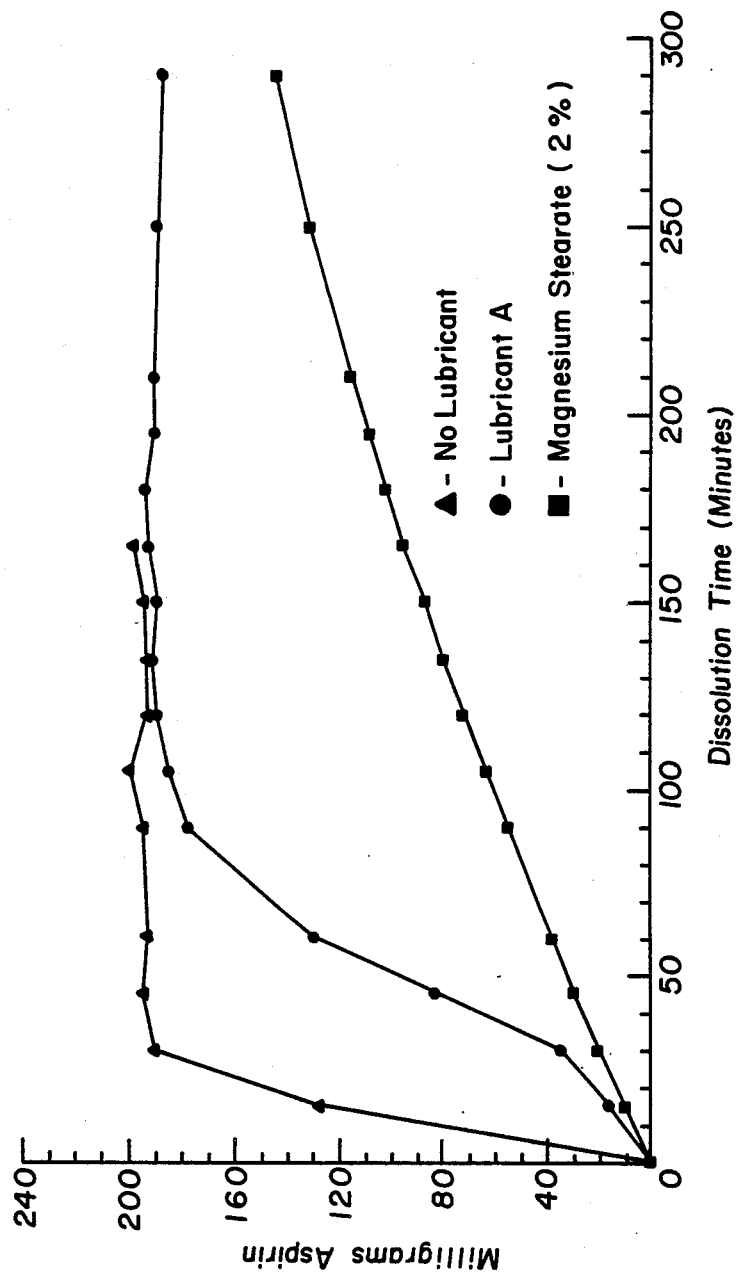
FIG. 2 is a graph showing a comparison of the lubricant used in the present invention with use of a conventional lubricant and no lubricant at all.

The results from dissolution analysis can be seen in FIG. 2. FIG. 2 shows the release of aspirin versus time for tablets containing 2% magnesium stearate and Lubricant A. As can be seen from the release profiles, tablets made with Lubricant A reach 100% dissolution at 90 minutes whereas the tablets made with 2% magnesium stearate never quite reach 100% dissolution after 300 minutes. The tablets made with Lubricant A take approximately 40 minutes longer to reach 100% dissolution than the control tablets. This is not a big disadvantage for Lubricant A due to the fact that it would be impossible to maintain tablet press tooling without a proper lubricant.

Results indicate that Lubricant A functions as a lubricating agent by reducing the friction at the tablet surface/die wall interface. Tablet hardness is not jeopardized by increasing the level of the lubricant over what is normally thought of as adequate for most tableting operations (0.25-1.0%). When working with tablet formulations where a disintegrant cannot be used due to incompatibility, Lubricant A functions as a lubricant without retarding the dissolution of the tablet. Comparisons between Lubricant A and magnesium stearate, the most popular commercially available tablet lubricant, have shown Lubricant A to be superior to magnesium stearate in all phases of the tableting operation covered in this report.

Tests are also run using Lubricants B, C and D, to show that the three components of the lubricant may be varied in concentration. When these concentrations are varied as indicated in the table and tests similar to those described above are run, similar physical and processing properties are obtained.

TABLE I

| Material | Percentage |
|---|---|
| Acetylsalicylic Acid, #40 Mesh | 81.25 |
| Microcrystalline Cellulose | 11.30 |
| Starch | 4.35 |
| Silica | 0.65 |
| Cellulose Gum | 2.00 |
| Lubricant A | 0.45 |

TABLE II

| Material | Percentage |
|---|---|
| Acetylsalicylic Acid, #40 Mesh | 50.0 |
| Dicalcium Phosphate | 30.0 |
| Microcrystalline Cellulose | 18.0 |
| Lubricant A/Magnesium Stearate | 2.0 |

TABLE III

Tablet Lubrication Evaluation

| Lubricant | Final Compression | Ejection Pressure | Hardness |
|---|---|---|---|
| Lubricant A | 2,500 lb | None | 6.6 KP |
| Magnesium Stearate | 8,250 lb | 16 lb | 7.2 KP |
| No Lubricant | 2,400 lb | 90 lb | 6.0 KP |

Lubricant A also assists in preparation of an elegant and acceptable tablets of acetaminophen, which is known in the industry to be one of the most difficult drug powders for direct compression. The tablets produced, using 1–2% Lubricant A, are hard, with least friability, without interference with the dissolution and disintegration, allowing compression at different pressures without affecting ejection strain on the punches.

An ideal lubricant should promote good mixing of the powder, reduce the ejection force to the level of 40–70 lb., decrease the friability of the tablets at various compression force to the level of 0–1%, and promote good hard tablets without impeding the dissolution and disintegration.

Although magnesium stearate is a commonly used lubricant in the pharmaceutical industry, it is well known to interfere with the disintegration and dissolution of the tablets, and some time catalyzes the degradation of some medicaments, and often leads to capping problem. No acceptable tablets are found to result from a mixture of acetaminophen and MCC. When flow aids are added, the tablets can be compressed, but the ejection forces were higher (100–200 lbs). Magnesium stearate does not help the flow or ejection in this case. High percentages of magnesium stearate interfere with disintegration and dissolution.

Use of 1–2% Lubricant A not only improves the flow, but permits the manufacturing of acceptable tablets with very low friability (0–0.5%). There is no effect on dissolution or disintegration, which is a rather remarkable observation.

The friability of acetaminophen tablets using magnesium stearate as a lubricant range between 2–100%, which is unacceptable. Essentially no usable tablets resulted without force feeding and without addition of a flow aid.

Although the ejection forces observed with tablets made using magnesium stearate are within the normal range, it is meaningless as the tablets are very soft and unusable with excessive friability. At 0.5% level, Lubricant A did assist in preparation of acceptably hard tablets, but the ejection forces are quite high, indicating its unsuitability for large scale production at that level. However, at 1–2% level of Lubricant A the ejection forces observed are normal even at high compression forces ranging between 1,000–4,500 lbs. At 1%, Lubricant A appears to be adequate for making tablets without unreasonable strain on the punches. If Lubricant A concentration is increased to 5% level, sticking problems are encountered, perhaps, due to melting of Lubricant A at high heat of compression. Sticking problems lead to rejection of the batches.

The hardness of acetaminophen tablets made with the help of Lubricant A as a lubricant, is comparable to those made by force feeding the mixture of acetaminophen, MCC and magnesium stearate. The tablets are hard, but disintegrate within a few seconds to a minute.

Unless otherwise indicated, all parts, percentages, ratios, etc. are by weight.

The invention has been described in detail with particular reference to preferred embodiments thereof, but it will be understood that variations and modifications can be effected within the spirit and scope of the invention.

We claim:

1. A formulation in powder form and adapted to be formed and compressed into tablets comprising an active ingredient and from about 0.5 to about 5.0%, based on the total weight of the formulation, of a lubricant which comprises
    (a) about 20–40% by weight of monoglycerides having an iodine value of about 2–15,
    (b) about 40–70% by weight of propylene glycol monoesters, and
    (c) about 5–20% by weight of a salt of a fatty acid ester of lactylic acid.

2. A formulation according to claim 1 wherein said active ingredient is a medicament or nutrient.

3. A formulation according to claim 1 wherein said lubricant comprises about 25–35% monoglycerides, about 50–60% propylene glycol monoesters and about 12–18% of said salt, all based on the total composition weight.

4. A tablet comprising the formulation of claim 1.
5. A tablet comprising the formulation of claim 2.
6. A tablet comprising the formulation of claim 3.

* * * * *